US00PP14107P39

(12) United States Plant Patent
Zerr

(10) Patent No.: US PP14,107 P3
(45) Date of Patent: Aug. 26, 2003

(54) POINSETTIA PLANT NAMED 'FISVINCI'

(75) Inventor: Katharina Zerr, Höhr-Grenzhausen (DE)

(73) Assignee: Florfis Ag, Binningen (CH)

( * ) Notice: Subject to any disclaimer, the term of this patent is extended or adjusted under 35 U.S.C. 154(b) by 0 days.

(21) Appl. No.: 10/108,705

(22) Filed: Mar. 29, 2002

(65) Prior Publication Data

US 2002/0157155 P1 Oct. 24, 2002

(30) Foreign Application Priority Data

Apr. 23, 2001 (EP) ..... 2001/0722

(51) Int. Cl.[7] ..... A01H 5/00
(52) U.S. Cl. ..... Plt./303
(58) Field of Search ..... Plt./303

*Primary Examiner*—Bruce R. Campell
*Assistant Examiner*—June Hwu
(74) *Attorney, Agent, or Firm*—Foley & Lardner

(57) ABSTRACT

A new and distinct poinsettia plant named 'Fisvinci' characterized by salmon-pink main bract color, slightly freckles with pink; ovate-shaped bracts with distinct lobes; dark green foliage with distinct, pointed lobes; medium sized, round, well-branched plant habit, with mostly upright directed branches; relatively early flowering response; and good performance in early culture at high temperatures.

1 Drawing Sheet

Latin name of the genus and species of the plant claimed: *Euphorbia pulcherrima.*
Variety denomination: 'Fisvinci'

BACKGROUND OF THE INVENTION

The present invention relates to a new and distinct cultivar of poinsettia plant known by the cultivar name 'Fisvinci' and botanically known as *Euphorbia pulcherrima*. 'Fisvinci' is a product of a planned breeding program which had the objective of creating new poinsettia cultivars with yellow to salmon flower color in combination with dark-green foliage and good cultivation ability. 'Fisvinci' originated from a hybridization program by Katharina Zerr, the inventor, in Hillscheid, Germany, in 1996.

The female parent was a proprietary hybrid seedling, no. S90-602-1 (unpatented) characterized by light salmon-pink bract color, medium green foliage, and medium-sized, wide, and bushy plant habit. The male parent was a hybrid seedling, no. S90-502-1(unpatented), having red bract color, dark green foliage, and early flowering.

The seeds germinated in the spring of 1997, and the resulting seedlings were identified by numbers. In the summer of 1997, a cutting was taken from each seedling, rooted and grown out for examination as flowering single-stem plants. 'Fisvinci' was discovered and selected as one flowering plant (no. 6876) within the progeny of the stated hybridization program by Katharina Zerr in the fall of 1997.

After this plant had been chosen, more cuttings were taken from the original seedling and grafted on rootstocks of the variety 'Beckmann's Altrosa' (U.S. Plant Pat. No. 9,336), in order to transmit the branching causing agent, phytoplasma, into the clone to improve the branching characteristics. From the upper area of the successfully grafted plants, shoot tip cuttings were taken for the cultivation of branched plants for the second examination in the fall of 1998.

Horticultural examination of the plant starting in 1998 and continuing has demonstrated that the combination of characteristics as herein disclosed for 'Fisvinci' are firmly fixed and retained through successive generations of asexual reproduction.

SUMMARY OF THE INVENTION

The following traits have been repeatedly observed and are determined to be basic characteristics of 'Fisvinci' which in combination distinguish this Poinsettia as a new and distinct cultivar:

1. salmon-pink main bract color, slightly freckled with pink;
2. ovate-shaped bracts with distinct lobes;
3. dark green foliage with distinct, pointed lobes;
4. medium sized, round, well-branched plant habit, with mostly upright directed branches;
5. relatively early flowering response; and
6. good performance in early culture at high temperatures.

'Fisvinci' has not been observed under all possible environmental conditions. The phenotype may vary significantly with variations in environment such as temperature, light intensity, and daylength. The following observations, measurements and comparisons describe plants grown in Hillscheid, Germany, under greenhouse conditions which approximate those generally used in commercial practice.

Of the many commercial cultivars known to the inventor, the most similar in comparison to 'Fisvinci' is the patented cultivar 'Fiscor Candy' (U.S. Plant Pat. No. 11,593).

In comparison to 'Fiscor Candy', 'Fisvinci' has a more intense salmon-pink main bract color, though with a similar kind of pink freckles. Bracts and leaves of 'Fisvinci' have more distinct and pointed, not rounded, lobes; and plant habit is round, more upright, less wide, and well-branched, even under unfavorable conditions after pinching. Additionally, 'Fisvinci' has a better performance in early culture at high temperature, because it is less susceptible to "heat delay".

BRIEF DESCRIPTION OF THE DRAWING

The accompanying color photographic drawing shows typical inflorescence and foliage of 'Fisvinci' with colors being as true as possible with illustrations of this type. The photograph shows a mature potted plant.

DETAILED BOTANICAL DESCRIPTION

The plants described were grown in a greenhouse in Langley, British Columbia, Canada, in the fall of 2001. Rooted cuttings were planted into 6 inch pots on July 18, and were pinched on August 13, leaving 7 leaves. Initially, the temperature was between 22° C. (minimum) and 24.5° C. (maximum or ventilation temperature), from September to late October between 18° and 21° C., and 15° to 17° C. in November. The plants initiated flowers under short-day conditions after applying shading (black-out) from September 10 to the end of September.

Observations and measurements were mainly taken around November 18, when the plants were 17.5 weeks old and had started flowering.

In the following description color references are made to The Royal Horticultural Society Colour Chart (R.H.S.). The color values were determined indoors in a north light.

Classification:
- *Botanical.*—*Euphorbia pulcherrima.*
- *Commercial.*—Poinsettia, cv. Fisvinci.

Parentage:
- *Female parent.*—Seedling S90-602-1.
- *Male parent.*—Seedling S90-502-1.

Plant:
- *Form.*—Shrub, self-branching.
- *Growth habit.*—Medium tall, with upright branches directed at an acute angle to the main stem; pinched plants are bushy and round in shape.
- *Height* (*above soil line*).—30.2 cm.
- *Width.*—53.0 cm.
- *Average number of branches.*—8.0.
- *Average number of inflorescences.*—7.2.
- *Stem color.*—Light green, RHS 143 B to RHS 144 A.
- *Rooting.*—Fast to medium, sufficiently rooted for transplanting after about 20 days in a greenhouse at a temperature of 22–24° C.
- *Blooming habit.*—Begin (under the culture regime described): botanically (cyathia open): around November 20; commercially (bracts colored, marketable): in mid November.
- *Flowering response time.*—About 8.5 weeks.
- *Natural flowering season.*—Beginning late November.
- *Keeping quality.*—Good quality will be maintained for at least 5 to 6 weeks.

Foliage:
- *Shape.*—Broad elliptical, rounded to obtuse base, distinct lobes with pointed tips, and apex acuminate.
- *Margin.*—Entire, apart from the lobes.
- *Texture.*—Upper surface: Smooth and flat, only weakly veined, color of the veins: whitish-green, RHS 145 A. Lower surface: Flat and smooth, except for the slightly protruding midrib and finer side veins in a pinnate pattern, the vein color is RHS 145 C.
- *Size.*—Leaf blade: Length: 11.30 cm. Width: 9.05 cm. Petiole: Length: 4.5 to 5.5 cm.
- *Quantity.*—About 40 leaves per plant.
- *Color.*—Generally dark green, uniform. Mature foliage: Upper surface RHS 139 A. Under surface RHS 137 A. New foliage: Upper side RHS 143 A. Under side RHS 144 A.
- *Leaf petiole.*—Upper side RHS 145 B, weak pink infusion may occur approximately RHS 49B, lower side RHS 145 C.
- *Aspect.*—The petioles are horizontally directed, with the leaf blades showing somewhat downward.

Disease resistance: No special observations made.

Flowering description: Whole inflorescence with surrounding bracts: somewhat over medium sized, star-shaped, with the bracts horizontally or slightly upwards directed.
- *Diameter.*—28–30 cm.
- *Number of bracts per inflorescence.*—About 12–14.
- *Keeping quality.*—Good, especially for an early flowering cultivar, no drooping of bracts, no fading of color Bracts:
- *Shape.*—Ovate, with acute to rounded base, distinct lobes with pointed tips, and with acuminate apex. Size of the largest fully colored bract: 15.0 cm long, 10.1 cm wide.
- *Surface texture.*—Flat and smooth, with the veins hardly visible. As bracts mature, the surface may appear slightly wrinkled or rugose.
- *Vein color.*—Upper side: Corresponds closely to the bract color. Lower side: Light green RHS 145 B.
- *Color.*—Generally salmon-pink, with pink freckles. Upper surface: Approximately RHS 41 D to 43 D, freckles RHS 44 D; lower bracts RHS 32 D Lower surface: RHS 41 C to 41 D, with freckles RHS 46 D — less distinct than on the upper surface.
- *Petiole.*—About 20 mm long, color upper and lower side: light green RHS 145 C, upper side partly brownish-pink infused near the leaf base: RHS 48 B.

Cyme: About 10 cyathia borne in a tight cluster, 20–22 mm in diameter.

Cyathium: Ovate, about 6 mm in diameter, mainly green colored, RHS 143 C, light greenish-yellow, RHS 150 A at the top end.

Peduncle: Light green, RHS 144 C, about 5 mm long.

Nectar cups: Usually one per cyathium, 5 mm wide, yellow colored, RHS 12 A.

Reproductive organs:
- *Stamens.*—About 20 per cyathium, cream colored filaments, RHS 11 D. Moderate pollen: yellow, RHS 12 A.
- *Pistil.*—1 per cyathium, light green style, RHS 145 A; stigma: lower side light green (like the pistil), RHS 145 A, upper side deep red, RHS 46 A, trifurcate, 6-lobed.
- *Ovaries.*—Medium green, RHS 143 B, initially obovate, diameter 3–4, 5 mm long, later triangular, 3 ovules.
- *Fruit/seed set.*—No observation to date.

I claim:

1. A new and distinct cultivar of Poinsettia plant named 'Fisvinci', as illustrated and described herein.

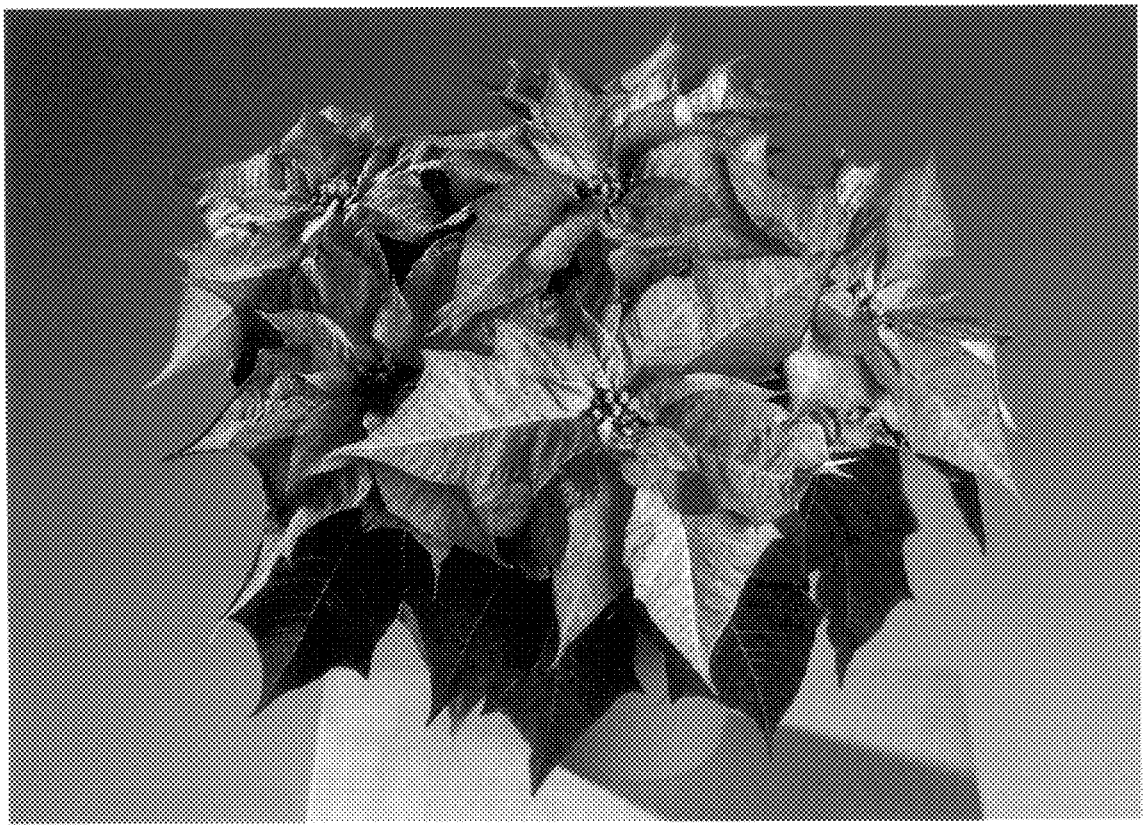

* * * * *